US00PP14653P29

(12) United States Plant Patent
Vandenberg

(10) Patent No.: US PP14,653 P2
(45) Date of Patent: Mar. 30, 2004

(54) CHRYSANTHEMUM PLANT NAMED 'CORAL FICTION'

(50) Latin Name: *Chrysanthemum×morifolium*
Varietal Denomination: Coral Fiction

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/452,074

(22) Filed: Jun. 2, 2003

(51) Int. Cl.[7] ..... A01H 5/00
(52) U.S. Cl. ..... Plt./286
(58) Field of Search ..... Plt./286

*Primary Examiner*—Anne Marie Grunberg
(74) *Attorney, Agent, or Firm*—C. A. Whealy

(57) ABSTRACT

A distinct cultivar of Chrysanthemum plant named 'Coral Fiction', characterized by its upright plant habit; freely flowering habit; daisy-type inflorescences that are about 6.7 cm in diameter; attractive yellow and red bi-colored ray florets and light green to bright yellow-colored disc florets; response time about 61 days; dark green foliage; strong peduncles; and excellent postproduction longevity with inflorescences and foliage maintaining good substance and color for about 21 days in an interior environment.

2 Drawing Sheets

Botanical classification/cultivar designation: *Chrysanthemum×morifolium* cultivar Coral Fiction.

BACKGROUND OF THE INVENTION

The present invention relates to a new and distinct cultivar of Chrysanthemum plant, botanically known as *Chrysanthemum×morifolium* and hereinafter referred to by the name 'Coral Fiction'.

The new Chrysanthemum is a product of a mutation breeding program conducted by the Inventor in Fort Myers and Alva, Fla. The objective of the program is to create new cut Chrysanthemum cultivars having inflorescences with desirable colors and good form and substance.

The new Chrysanthemum is a naturally-occurring whole plant mutation of a proprietary induced mutation that originated by exposing unrooted cuttings of the Chrysanthemum cultivar Fiction, disclosed in U.S. Plant Pat. No. 12,734, to X-ray radiation at a dose of 1,750 rads in Fort Myers, Fla. The new Chrysanthemum was discovered and selected by the Inventor as a single flowering plant within a population of plants of the irradiated selection in November, 1998 in Alva, Fla. The selection of this plant was based on its desirable inflorescence color and good form and substance.

Asexual reproduction of the new Chrysanthemum by terminal cuttings taken in a controlled environment in Alva, Fla. since March, 1999, has shown that the unique features of this new Chrysanthemum are stable and reproduced true to type in successive generations.

SUMMARY OF THE INVENTION

Plants of the cultivar Coral Fiction have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Coral Fiction'. These characteristics in combination distinguish 'Coral Fiction' as a new and distinct cultivar:

1. Upright cut Chrysanthemum that is usually grown as a natural spray.
2. Freely flowering habit, about eight inflorescences per flowering stem.
3. Daisy-type inflorescences that are about 6.7 cm in diameter.
4. Attractive yellow and red bi-colored ray florets and light green to bright yellow-colored disc florets.
5. Response time about 61 days.
6. Dark green foliage.
7. Strong peduncles.
8. Excellent postproduction longevity with inflorescences and foliage maintaining good substance and color for about 21 days in an interior environment.

Plants of the new Chrysanthemum are most similar to plants of the cultivar Fiction. In side-by-side comparisons conducted in Alva, Fla., plants of the new Chrysanthemum differed from plants of the cultivar Fiction in the following characteristics:

1. Plants of the new Chrysanthemum flowered later than plants of the cultivar Fiction.
2. Plants of the new Chrysanthemum and the cultivar Fiction differed in ray floret coloration as plants of the cultivar Fiction had white and purple bi-colored ray florets.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Coral Fiction' grown as a natural spray.

The photograph on the second sheet comprises a close-up view of a typical flowering stem of 'Coral Fiction' grown as a natural spray.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Madrid, Cundinamarca, Colombia, South America, under conditions which approximate commercial practice in a single-layer polyethylene-covered greenhouse. Two-week old rooted cuttings were planted on Jan. 2, 2003 and received 17 long day/short nights followed by short day/long nights until flowering. Plants were grown as single-stem natural spray cut Chrysanthemums. During the production time, the following environmental conditions were measured: day temperatures, 19 to 24° C.; night temperatures, 4 to 12° C.; and light levels, 3,000 to 5,000 foot-candles. Measurements and numerical values represent averages for six to ten typical flowering stems and were taken about ten weeks after the start of short days.

Botanical classification: *Chrysanthemum×morifolium* cultivar Coral Fiction.

Commercial classification: Daisy-type cut Chrysanthemum.

Parentage: Naturally-occurring whole plant mutation of a proprietary *Chrysanthemum×morifolium* induced mutation, not patented.

Propagation:

*Type.*—Terminal tip cuttings.

*Time to rooting.*—About 10 to 14 days with soil temperatures of 18 to 21° C.

*Root description.*—Fine, fibrous and well-branched.

Plant description:

*Appearance.*—Herbaceous daisy-type cut flower that is typically grown as a natural spray.

*Flowering stem description.*—Aspect: Erect. Length: About 102 cm. Diameter (natural spray diameter): About 17 cm. Diameter (base of stem): About 5.5 mm. Internode length: About 4.5 cm. Texture: Pubescent; longitudinally ridged. Color: 146A.

*Foliage description.*—Arrangement: Alternate. Length: About 5.75 cm. Width: About 3.75 cm. Apex: Mucronate. Base: Truncate. Margin: Palmately lobed; sinuses parallel to convergent. Texture: Upper and lower surfaces pubescent; smooth and leathery; veins prominent on lower surface. Color: Developing foliage, upper surface: Darker green than 147A. Developing foliage, lower surface: Darker green than 147B. Fully expanded foliage, upper surface: 147A. Fully expanded foliage, lower surface: Slightly darker green than 147B. Venation, upper and lower surfaces: 147B. Petiole: Length: About 1.2 cm. Diameter: About 2 mm. Color: Upper surface: 146B. Lower surface: Close to 146B.

Flowering description:

*Appearance.*—Daisy-type inflorescence form with elongated oblong-shaped ray florets. Inflorescences borne on terminals, arising from leaf axils. Disc and ray florets develop acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 61 days later when grown as a natural spray.

*Postproduction longevity.*—In an interior environment, inflorescences and foliage will maintain good color and substance for about 21 days in an interior environment.

*Quantity of inflorescences.*—Freely flowering habit, about eight inflorescences per stem develop.

*Inflorescence size.*—Diameter: About 6.7 cm. Depth (height): About 1 cm. Diameter of disc: About 1.6 mm. Diameter of receptacle: About 5 mm.

*Inflorescence buds.*—Shape: Oblate. Height: About 5 mm. Diameter: About 7 mm. Color: Close to 147A.

*Ray florets.*—Shape: Elongated oblong; slightly concave to flat. Length: About 3.3 cm. Width: About 1 cm. Corolla tube length: About 2.5 mm. Apex: Acute to emarginate. Base: Fused. Texture: Smooth, velvety, glabrous; longitudinally ridged. Aspect: Initially upright; when mature, perpendicular to the peduncle. Number of ray florets per inflorescence: About 32 aged in one or two rows. Color: When opening and fully opened, upper surface: 5A to 6A; towards the apex, overlain with 46A to 53A. When opening and fully opened, lower surface: 5C to 5D; towards the apex, underlain with 53A.

*Disc florets.*—Shape: Tubular, elongated. Length: About 5 mm. Width: Apex: About 1.5 mm. Base: About 1 mm. Number of disc florets per inflorescence: About 148. Color: Immature: 144A. Mature: Apex: 9A. Mid-section: Close to 144A. Base: Close to 155D.

*Phyllaries.*—Quantity per inflorescence: About 28. Length: About 6 mm. Width: About 1.5 mm. Shape: Lanceolate to deltoid. Apex: Acute. Base: Truncate. Margin: Entire. Texture, upper surface: Smooth, waxy. Texture, lower surface: Pubescent. Color, upper surface: Darker green than 146A. Color, lower surface: Close to 147A.

*Peduncles.*—Length: First peduncle: About 9.75 cm. Fourth peduncle: About 16 cm. Seventh peduncle: About 19.5 cm. Diameter: About 2 mm. Angle: About 40° from vertical. Strength: Strong. Texture: Pubescent. Color: 146A.

*Reproductive organs.*—Androecium: Present on disc florets only. Anther color: 12A to 15A. Amount of pollen: None observed. Gynoecium: Present on both ray and disc florets.

*Seed/fruit.*—Seed and fruit production has not been observed.

Disease/pest resistance: Resistance to pathogens and pests common to Chrysanthemums has not been observed on plants grown under commercial conditions.

Temperature tolerance: Plants of the new Chrysanthemum have demonstrated good tolerance to low temperatures of 5° C. and high temperatures high temperatures of 35° C.

It is claimed:

1. A new and distinct cultivar of Chrysanthemum plant named 'Coral Fiction', as illustrated and described.

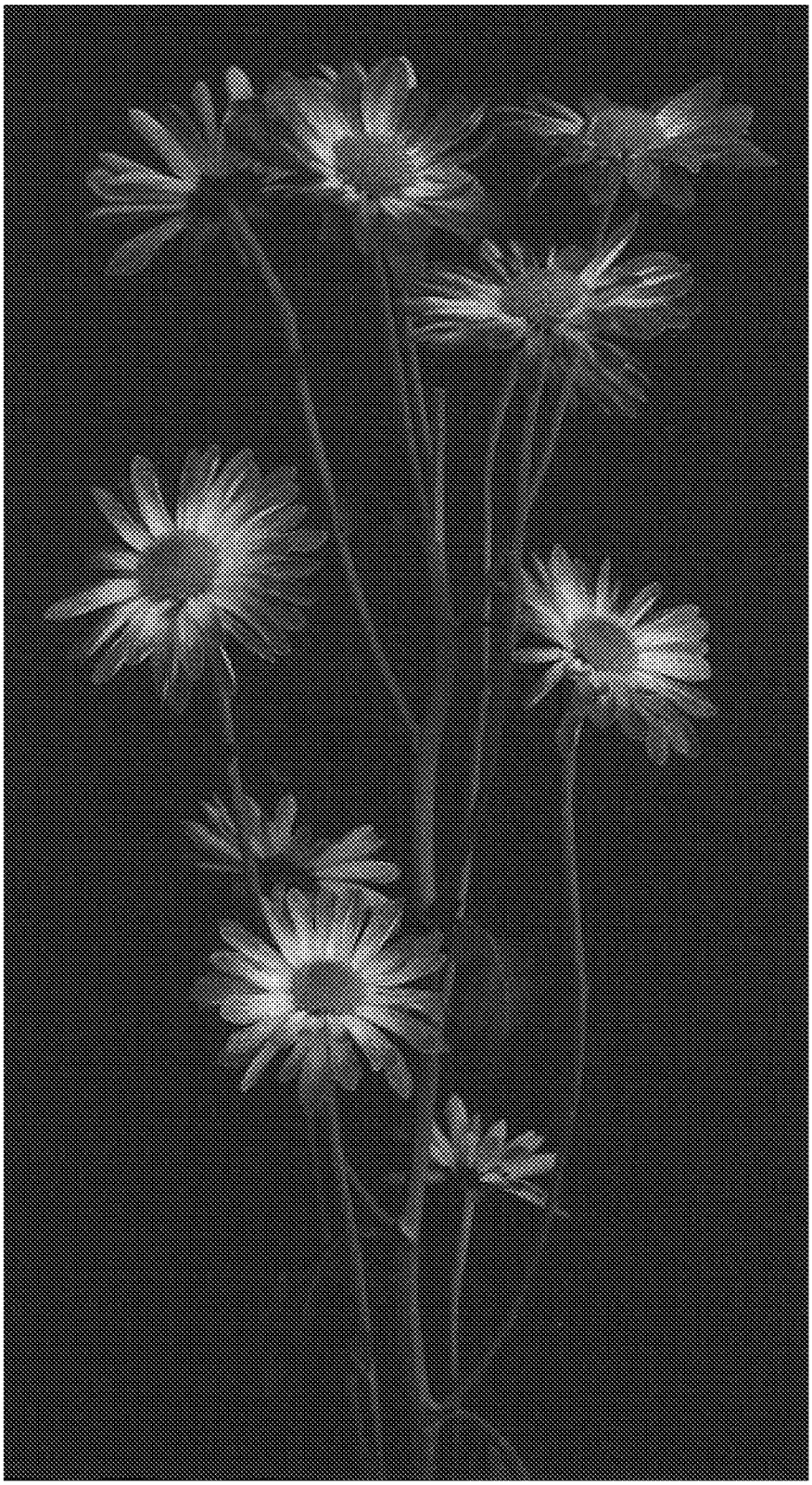

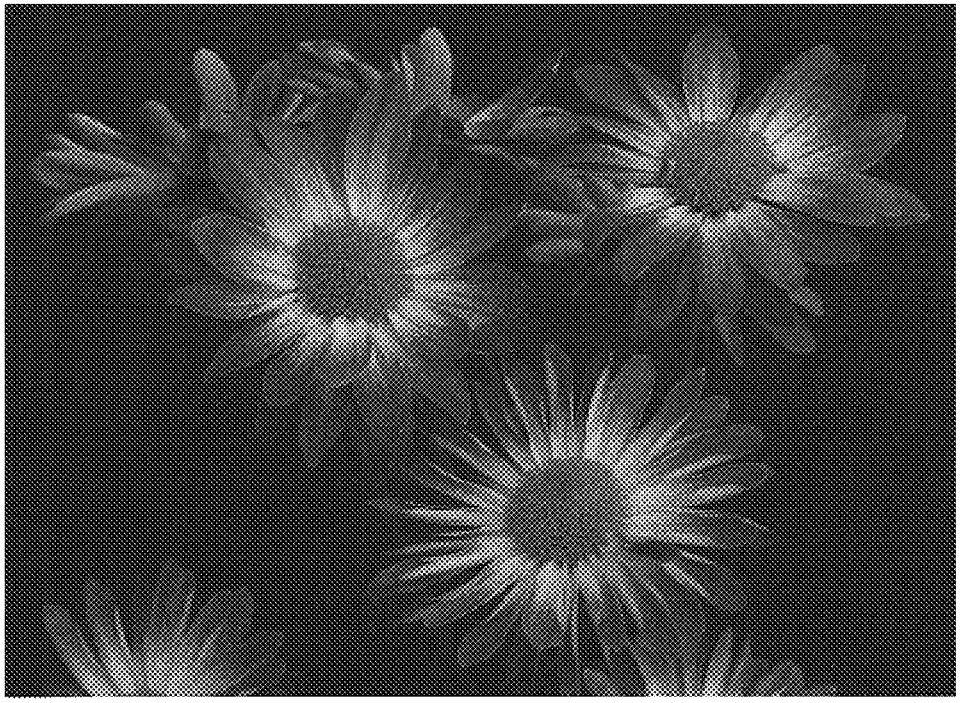

* * * * *